US009208286B2

(12) United States Patent
Chou (10) Patent No.: US 9,208,286 B2
(45) Date of Patent: Dec. 8, 2015

(54) METHOD FOR TRANSMITTING PHYSIOLOGICAL DETECTION SIGNALS THROUGH MOBILE PHONE DEVICE VIA BLUETOOTH/WI-FI COMMUNICATION SYSTEM (71) Applicant: Yuan-Hsiang Chou, Taipei (TW)

(72) Inventor: Yuan-Hsiang Chou, Taipei (TW)

( * ) Notice: Subject to any disclaimer, the term of this patent is extended or adjusted under 35 U.S.C. 154(b) by 71 days.

(21) Appl. No.: 14/093,017

(22) Filed: Nov. 28, 2013

(65) Prior Publication Data

US 2014/0148138 A1 May 29, 2014

(30) Foreign Application Priority Data

Nov. 29, 2012 (TW) .............................. 101144837 A (51) Int. Cl.
G06F 15/16 (2006.01)
G06F 19/00 (2011.01)
H04W 4/12 (2009.01)
H04W 4/00 (2009.01)

(52) U.S. Cl.
CPC ........... *G06F 19/3418* (2013.01); *H04W 4/008* (2013.01); *H04W 4/12* (2013.01)

(58) Field of Classification Search
None
See application file for complete search history.

(56) References Cited

U.S. PATENT DOCUMENTS

| 5,416,695 A * | 5/1995 | Stutman ................ A61B 5/1112 379/38 |
| 8,842,001 B2 * | 9/2014 | Gilham .................. A61B 5/746 340/539.1 |
| 9,135,398 B2 * | 9/2015 | Kaib .................... G06F 19/3418 |
| 2005/0113650 A1 * | 5/2005 | Pacione ................. A61B 5/411 600/300 |
| 2005/0114170 A1 * | 5/2005 | Park ....................... G06F 19/322 705/2 |
| 2006/0063980 A1 * | 3/2006 | Hwang et al. ................. 600/300 |
| 2007/0027367 A1 * | 2/2007 | Oliver .................. A61B 5/0002 600/300 |
| 2007/0106133 A1 * | 5/2007 | Satchwell et al. ............ 600/309 |
| 2007/0227367 A1 * | 10/2007 | Antal et al. ..................... 99/426 |
| 2007/0253021 A1 * | 11/2007 | Mehta .................. A61B 5/0002 358/1.15 |
| 2008/0154099 A1 * | 6/2008 | Aspel ................... G06F 19/3418 600/301 |
| 2009/0240119 A1 * | 9/2009 | Schwaibold et al. ......... 600/301 |
| 2010/0106519 A1 * | 4/2010 | Lemke et al. ..................... 705/2 |
| 2010/0249541 A1 * | 9/2010 | Geva .................... G06F 19/3418 600/301 |
| 2011/0077965 A1 * | 3/2011 | Nolte ..................... G06Q 10/10 705/3 |
| 2012/0226117 A1 * | 9/2012 | Lamego et al. ............... 600/316 |
| 2012/0226771 A1 * | 9/2012 | Harrington et al. ........... 709/217 |
| 2014/0081087 A1 * | 3/2014 | Yu .................................. 600/301 |
| 2014/0081100 A1 * | 3/2014 | Muhsin et al. ................ 600/324 |
| 2014/0081662 A1 * | 3/2014 | Bradrick et al. .................. 705/3 |
| 2014/0275876 A1 * | 9/2014 | Hansen et al. ................ 600/323 |
| 2015/0079908 A1 * | 3/2015 | Schmitt ........................ 455/41.2 |

* cited by examiner

Primary Examiner — Kenny Lin (57) ABSTRACT

A method for transmitting physiological detection signals through a mobile phone device via a Bluetooth/Wi-Fi communication system includes steps of providing at least a physiological signal detector for performing a physiological examination on a subject so as to generate at least one physiological detection signal which is transmitted to a built-in Bluetooth/Wi-Fi module of a mobile phone of a subject through a communication interface and a Bluetooth/Wi-Fi module at a detection end. The physiological detection signal is encoded by the mobile phone of the subject to be a message or a signal code containing a data transmission command and a data format protocol and is transmitted to a mobile phone or an App ID of a remote caretaker, so that the caretaker is able to instantly control a physiological state of the subject.

13 Claims, 7 Drawing Sheets

S21 — The physiological signal detector transmits the physiological detection signal being measured to the Bluetooth module at the detection end according to a command.

S22 — The physiological signal detector transmits a message containing the phone number of the caretaker to the Bluetooth module at the detection end.

S23 — Utilize the Bluetooth module at the detection end to transmit the message containing the phone number of the caretaker to the built-in Bluetooth module of the mobile phone of the subject S24 — The Bluetooth module at the detection end transmits the message incorporated with the physiological detection signal to the mobile phone of the caretaker.

S25 — Utilize the mobile phone of the subject to transmit the message incorporated with the physiological detection signal to the mobile phone of the caretaker.

S26 — The mobile phone of the subject sends an acknowledgement message to the physiological signal detector through the built-in Bluetooth module and the Bluetooth module at the detection.

METHOD FOR TRANSMITTING PHYSIOLOGICAL DETECTION SIGNALS THROUGH MOBILE PHONE DEVICE VIA BLUETOOTH/WI-FI COMMUNICATION SYSTEM

BACKGROUND OF THE INVENTION

1. Field of the Invention

The present invention relates to a method for transmitting physiological detection signals through a mobile phone device via a Bluetooth/Wi-Fi communication system, and particularly to a method for transmitting the physiological detection signals generated by a physiological signal detector for performing a physiological examination on a subject, with a data transmission command and a data format protocol based on a communication standard of ASCII, to a mobile phone of a remote caretaker in a manner of sending a message or an App ID message.

2. Related Art

With the increasing number of elderly individuals and chronic patients in the world population, how to utilize the limited medical resources to efficiently provide patients with instant medical care renders remote patient monitoring and nursing very significant. The remote patient monitoring is a remote interface that allows daily monitoring data of patients to be received and transmitted between home patients and remote caretakers. A remote monitoring system includes five major factors of a patient side, a monitoring device, a remote monitoring interface, a database of center service and clinical data, and medical staff and caretakers. However, such system needs to integrate the original medical system, the related industry and the information and communication technology (ICT) industry. Based on this fundamental concept, there are no complete criteria for industry integration interface for the industry to develop.

As is well known, since 1970 with the efforts of the government and industry advancers, the ICT industry in Taiwan has been developed for more than 40 years to be very mature, which must result in a slow development of the whole industry in the future, and the turnover and profits of the Taiwan ICT industry may be decreased because of the year-after-year decline of the average sales unit price. Therefore, domestic firms have endeavored to figure out countermeasures. The Taiwan ICT industry is completely linked by upstream, midstream, and downstream, with comprehensively provided components and cooperation of rapidly applying technical integration and high efficient production, and thus makes the Taiwan ICT firms have an important position in the market of the world.

However, there is still no unit standard of transmission of messages of the remote medical monitoring. Each supplier has its own product interface system and therefore cannot produce extensively product efficacy in the market. Consequently, if there is an easy and efficient standard platform for the ICT industry to combine with medical instruments for quickly and precisely sending messages to whom in need, the ICT industry and the remote medical monitoring system can be well developed.

SUMMARY OF THE INVENTION

Accordingly, an object of the present invention is to provide a method for transmitting physiological detection signals through a mobile phone device and a Bluetooth communication system.

To achieve the mentioned object, the method comprises:
providing at least one the physiological signal detector for performing a physiological examination on a subject so as to generate at least one physiological detection signal;
providing a communication interface for transmitting the physiological detection signal from the physiological signal detector to the Bluetooth module or the Wi-Fi module at a detection end;
the Bluetooth module or the Wi-Fi module at the detection end being intended to transmit the physiological detection signal;
utilizing a mobile phone equipped with a built-in Bluetooth module or a built-in Wi-Fi module of the subject to receive the physiological detection signal; and
creating a message containing a data transmission command and a data format protocol by encoding the physiological detection signal through the mobile phone of the subject, then transmitting the message to a mobile phone of a caretaker.

In this manner, the physiological detection signal is incorporated into the message or an application (App) identification (ID) message through the mobile phone of the subject, and the message is then transmitted to the mobile phone of the caretaker. The mobile phone of the subject further sends an acknowledgement message to the physiological signal detector through the Bluetooth module or the Wi-Fi module at the detection end for acknowledging that the physiological detection signal is being sent to the mobile phone of the caretaker.

Accordingly, the physiological signal detector is capable of automatically transmitting the message or the App ID message to the mobile phone of the remote caretaker through the Bluetooth module or the Wi-Fi module at the detection end, the communication interface, and the mobile phone of the subject as soon as the physiological detection signal is detected, so as to allow the caretaker to instantly control the physiological state of the subject.

In accordance with an embodiment of the present invention, a method of the present invention for transmitting physiological detection signals through a mobile phone device and a Wi-Fi communication system comprises: providing at least one the physiological signal detector for performing a physiological examination on a subject so as to generate at least one physiological detection signal;
providing a communication interface for transmitting the physiological detection signal from the physiological signal detector to the Bluetooth module or the Wi-Fi module at a detection end;
the Bluetooth module or the Wi-Fi module at the detection end being intended to transmit the physiological detection signal;
utilizing a mobile phone equipped with a built-in Bluetooth module or a built-in Wi-Fi module of the subject to receive the physiological detection signal; and
creating a signal code containing a data transmission command and a data format protocol by encoding the physiological detection signal through the mobile phone of the subject, then transmitting the signal to an App ID of a smartphone so as to be allowed to be downloaded to the mobile phone of the caretaker.

In this manner, the physiological detection signal is incorporated into the message or the signal code through the mobile phone of the subject, and the message is then transmitted to the App ID of the smartphone. The mobile phone of the subject further sends an acknowledgement message to the physiological signal detector through the Bluetooth module or the Wi-Fi module at the detection end for acknowledging that the physiological detection signal is being sent to the App ID of the smartphone.

In accordance with another embodiment of the present invention, the data transmission command and the data format protocol are created based on a communication standard of ASCII.

In accordance with another embodiment of the present invention, the data transmission command and the data format protocol comprise command initiation, command operation, and content format, the command initiation is intended to initiate operations of transmitting a message, transmitting a string, and transmitting physiological detection values including oximeter density, sphygmomanometer values, glucose meter values, and physiological detection signal.

In accordance with another embodiment of the present invention, the physiological signal detector is intended to enable the Bluetooth module at the detection end to detect the built-in Bluetooth module of the mobile phone of the subject, and the mobile phone of the subject is intended to enable the built-in Bluetooth module to detect the Bluetooth module at the detection end so as to allow the Bluetooth module at the detection end and the built-in Bluetooth module of the mobile phone of the subject to communicate with each other.

In accordance with another embodiment of the present invention, the Bluetooth module or the Wi-Fi module at the detection end, and the built-in Bluetooth module or the built-in Wi-Fi module are respectively communicated based on Standard BT 2.0+EDR Class II.

In accordance with another embodiment of the present invention, the communication interface is a universal asynchronous receiver/transmitter (DART).

Still in another embodiment of the present invention, the number of the physiological signal detector is more than one.

Accordingly, the method of the present invention utilizes the three interfere standards of the UART, the Bluetooth or Wi-Fi, and the mobile phone standard data to set a transmission platform for the physiological signal detector, so as to transmit the physiological detection signal being detected and measured in a manner of sending a message or a signal code to a receiving end of a target through the UART, the data transmission command and the data format protocol, the Bluetooth or Wi-Fi module, and the mobile phone device, without requiring additional data transmission apparatus.

Furthermore, the method of the present invention utilizes the UART standard, Bluetooth or Wi-Fi standard, and GSM standard, in combination with the Bluetooth module or the Wi-Fi module, and communication protocol, to transmit physiological values measured by the physiological signal detector in a manner of sending a message to a remote GSM mobile phone, or in a manner of sending a signal code to an App ID of a remote smartphone for being downloaded by a portable communication device.

DESCRIPTION OF THE PREFERRED EMBODIMENTS

Figure 1:
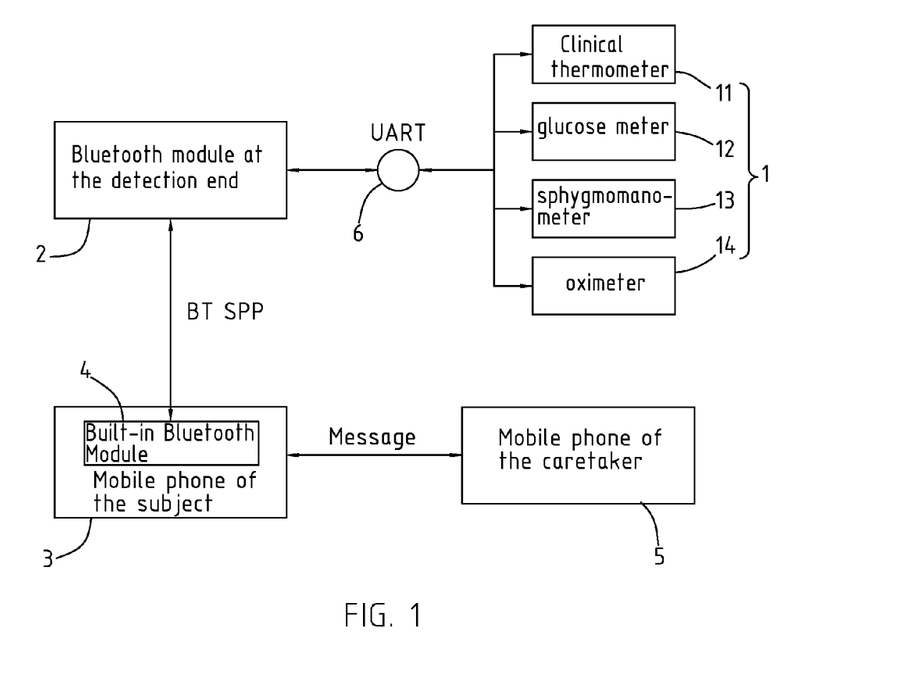
FIG. 1 is a schematic block diagram showing a configuration of a method in accordance with a first embodiment of the present invention.
Figure 2:
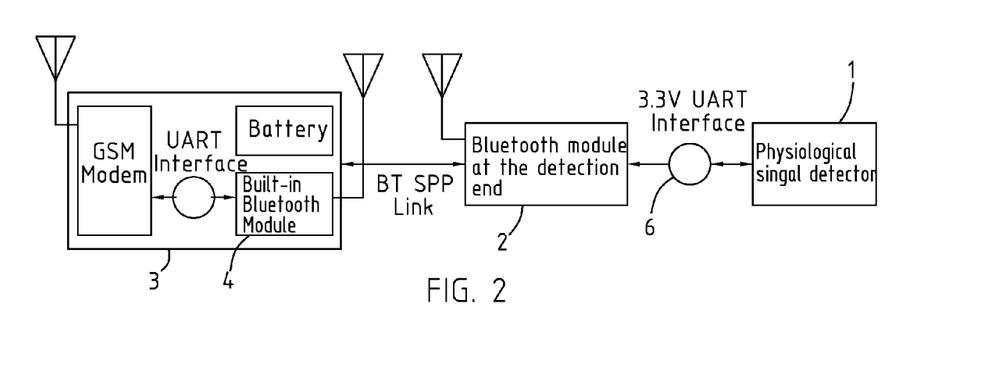
FIG. 2 is another schematic block diagram showing a configuration of the method in FIG. 1.

Referring to FIG. 1 showing a schematic block diagram which illustrates a configuration of a method in accordance with a first embodiment of the present invention, the method for transmitting physiological detection signals through a mobile phone device and a Bluetooth/Wi-Fi communication system comprises: providing a physiological signal detector 1, a communication interface, and a mobile phone 3 of a subject. Referring to FIG. 1 in combination with FIG. 3, the method of the present invention further comprises: providing a Bluetooth module 2 or a Wi-Fi module 2a at a detection end, a built-in Bluetooth module 4 or a Wi-Fi module 4a equipped in the mobile phone 3 of the subject, and a data transmission command and a data format protocol that are created based on a communication standard of ASCII.

Figure 3:
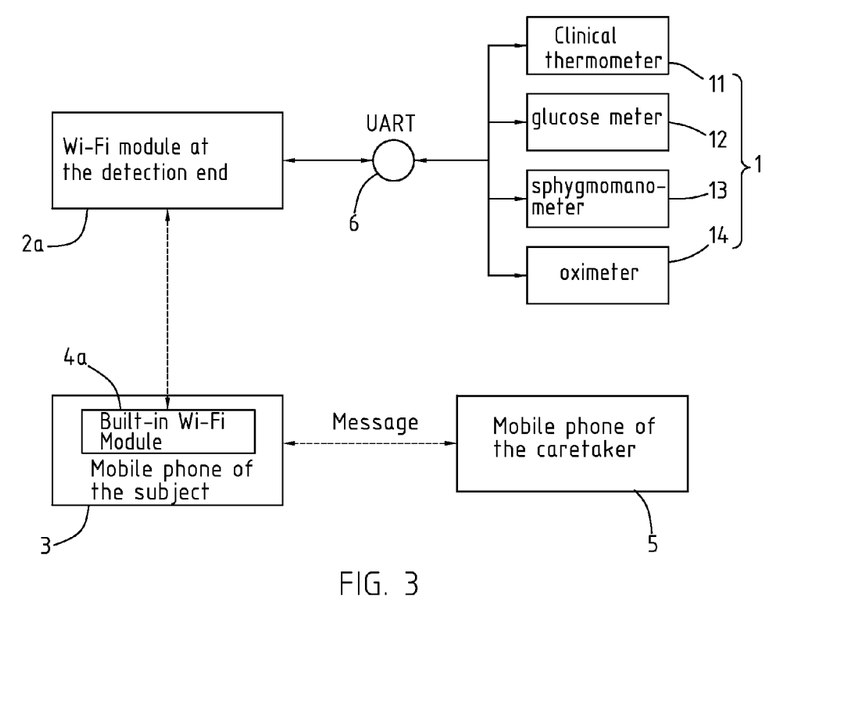
FIG. 3 is a schematic block diagram showing another example of the configuration of FIG. 1.
Figure 4:
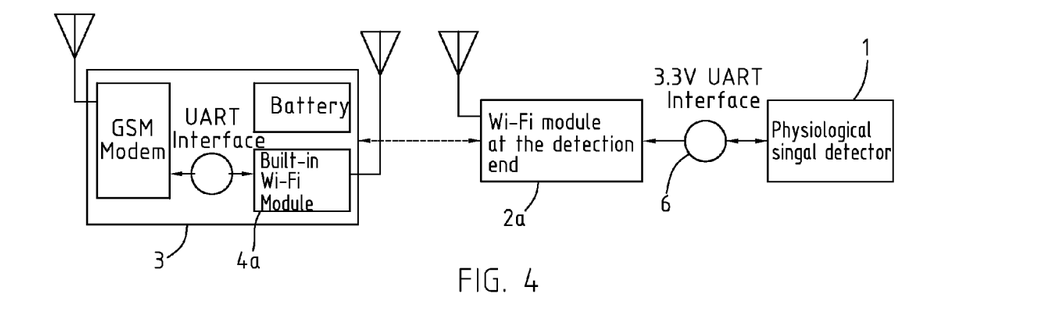
FIG. 4 is another schematic block diagram showing a configuration of the method in FIG. 3.

The physiological signal detector 1 is intended to perform a physiological examination on at least one subject so as to generate at least one physiological detection signal. The Bluetooth module 2 or the Wi-Fi module 2a at the detection end is electrically connected to the physiological signal detector 1. In this preferable embodiment, the communication interface is a universal asynchronous receiver/transmitter (UART) 6 which is electrically connected between the physiological signal detector 1 and the Bluetooth module 2 at the detection end. Alternatively, the UART 6 is electrically connected between the physiological signal detector 1 and the Wi-Fi module 2a at the detection end.

The physiological signal detector 1 is capable of transmitting the physiological detection signal to the Bluetooth module 2 or the Wi-Fi module 2a at the detection end through the UART 6, and then the physiological detection signal is being transmitted through the Bluetooth module 2 or the Wi-Fi module 2a at the detection end. In practice, the Bluetooth module 2 or the Wi-Fi module 2a at the detection end is capable of being installed in the physiological signal detector 1, or is electrically connected to the physiological signal detector 1 over a conductive wire.

The mobile phone 3 of the subject is a Global System for Mobile Communication (GSM) mobile phone. The built-in Bluetooth module 4 or the Wi-Fi module 4a is built in and connected to the mobile phone 3 of the subject.

The mobile phone 3 of the subject is capable of receiving the physiological detection signal through the built-in Bluetooth module 4 or the Wi-Fi module 4a, and is capable of creating a message containing a data transmission command and a data format protocol by encoding the physiological detection signal. The message or an application (App) identification (ID) message is then being sent to a GSM mobile phone 5 of a caretaker, so as to allow the mobile phone 3 of the subject to transmit the physiological detection signal to the mobile phone 5 of the caretaker or the App ID 7 of a smart phone in a manner of sending the message or the App ID message.

Number of the physiological signal detector 1 can be one or more than one, and the physiological signal detector 1 is a clinical thermometer 11, a glucose meter 12, a sphygmomanometer 13, a pulse meter, or an oximeter 14. Moreover, the physiological signal detector 1 is stored with a plurality of phone numbers of the mobile phone 5 of the caretaker. The above-mentioned message being sent is a message based on short message service (SMS).

The Bluetooth module 2 or the Wi-Fi module 2a at the detection end is communicated with the clinical thermometer 11, the glucose meter 12, the sphygmomanometer 13, the pulse meter, or the oximeter 14 though the UART 6.

The Bluetooth module 2 at the detection end and the built-in Bluetooth module 4 are respectively compatible with Standard BT 2.0+EDR Class II, and the Wi-Fi module 2a at the detection end and the built-in module 4a are respectively compatible with Standard BT 2.0+EDR Class II.

The Bluetooth module 2 at the detection end and the built-in Bluetooth module 4 respectively comprise: a microcontroller (MCU), a random access memory (RAM), a baseband DSP (digital signal processor), a UART interface based I/O, an X'TAL for system clock oscillator, a transmitting range at 2.4 GHz, and an external memory.

A frequency range of the Bluetooth module 2 and the built-in Bluetooth module 4 is ISM 2.4 GHz, frequency-hopping spread spectrum, which chops up the data being sent and transmits chunks of it on up to 79 bands (1 MHz each; centered from 2402 to 2480 MHz) in the range 2,400-2,483.5 MHz (allowing for guard bands).

A modulation of the Bluetooth module 2 and the built-in Bluetooth module 4 is performed at Gaussian frequency-shift keying (GFSK) data rate 1 Mbit/s π/4-DQPSK and 8DPSK data rate 2 and 3 Mbit/s (Enhanced Data Rate) Maximum Application Throughput 2.1 Mbit/s, as shown in the following table 1.

TABLE 1

Bluetooth modulation way and transmission rate

| Data Rate Scheme | Bits Per Symbol | Modulation |
|---|---|---|
| Basic Data Rate | 1 | GFSK |
| EDR | 2 | π/4 DQPSK |
| EDR | 3 | 8DPSK(optional) |

Basic Rate

| Access Code | Header | Payload | | | |
|---|---|---|---|---|---|

Enhanced Data Rate

| Access Code | Header | Guard | Sync | Payload | Trailer |
|---|---|---|---|---|---|

← π/4 DQPSK or 8DPSK →

Bluetooth power/distance class is shown in the following table 2.

TABLE 2

Bluetooth Class

| | Maximum Permitted Power | | Range |
|---|---|---|---|
| Class | mW | dBm | (approximate) |
| Class 1 | 100 | 20 | ~100 meters |
| Class 2 | 2.5 | 4 | ~10 meters |
| Class 3 | 1 | 0 | ~5 meter |

The above mentioned classes 1/2/3 are defined as a standard of power and distance of Bluetooth for various applications.

Figure 5:
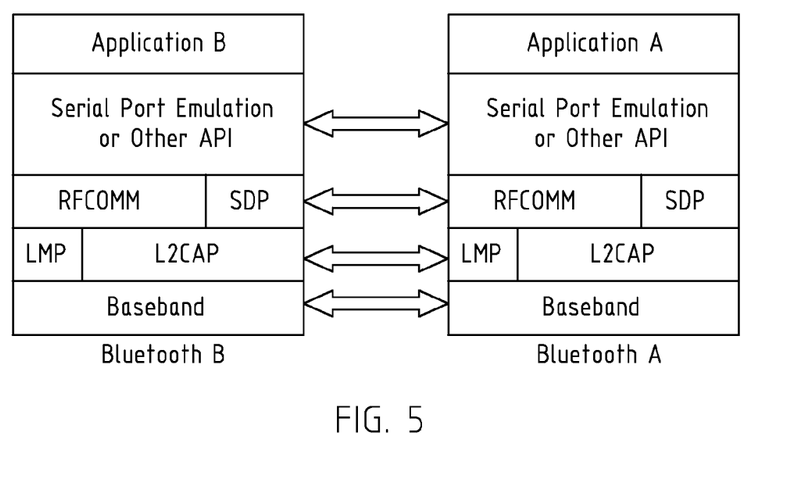
FIG. 5 is a schematic diagram showing a Bluetooth protocol stack of FIG. 1.

Please refer to FIG. 5 showing a block diagram of Bluetooth Protocol Stack of the Bluetooth module 2 and the built-in Bluetooth module 4 of the present invention, wherein the stack based on Bluetooth communication protocol is a standard of Bluetooth communication/interface.

LMP (Link Management Protocol)
L2CAP (Logical Link Control & Adaptation Protocol)
SDP (Service Discovery Protocol)
HCI (Host/Controller Interface)
RFCOMM (Radio Frequency Communications)
SPP (Serial Port Profile): SPP defines how to set up virtual serial ports and connect two Bluetooth enabled devices.

⅓ rate forward error correction (FEC) or ⅔ rate CRC will be retransmitted until acknowledged by automatic repeat request (ARQ).

The reason to adopt Standard BT 2.0+EDR Class II is because BT 2.0 is issued on 9 Jan. 2004, and is already adopted by current existed chipset manufacturers Broadcom and CSR. Additionally, relevant software and hardware interfaces compatible with such standard have already been developed, and therefore such standard is easily and directly adopted by the information and communication technology (ICT) industry and compatible with subsequently developed medical instruments. Considering power and 10 m available distance for home use, Class II is the most appropriate standard for use.

The reason to utilize the UART 6 as shown in FIG. 3 is because that current industry utilizes a micro controller which is equipped with the UART 6. The voltage and telecommunication specification are known to the current industry, and is easily and directly adopted by ICT industry and compatible with subsequently developed medical instruments.

TABLE 3

UART Character Framing

| Start bit | Bit 0 | Bit 1 | Bit 2 | Bit 3 | Bit 4 | Bit 5 | Bit 6 | Bit 7 | Stop bit |
|---|---|---|---|---|---|---|---|---|---|

The UART 6 is based on ASCII to transmit data, ASCII is the most common universal byte coding system and is equivalent to ISO/IEC 646. As stated above, the reason to adopt ASCII is because it is known to the industry and is easily and directly adopted by the ICT industry and subsequently developed medical instruments.

Figure 6:
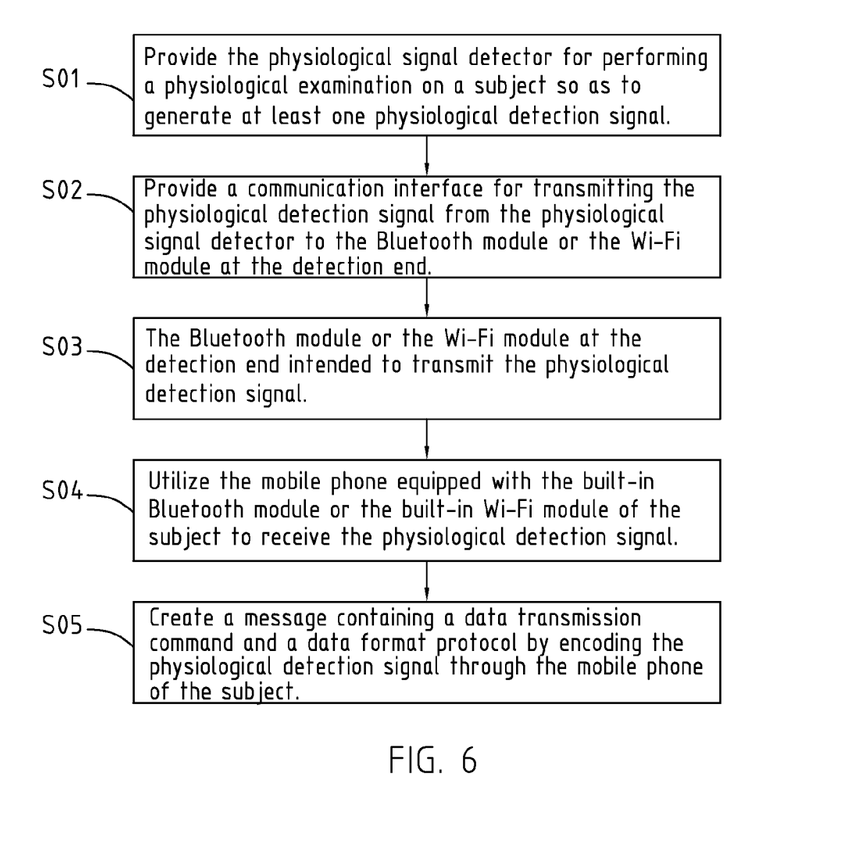
FIG. 6 is a schematic flow chart of the method of the present invention.

As shown in FIG. 6, with the combination of the above-mentioned Bluetooth module or the Wi-Fi module and the mobile phone, and a data transmission command and a data format protocol based on ASCII, the method of the present invention for transmitting physiological detection signals through a mobile phone device and a Bluetooth/Wi-Fi communication system comprises the following steps:

S01: providing at least one the physiological signal detector 1 for performing a physiological examination on a subject so as to generate at least one physiological detection signal;

S02: providing a communication interface for transmitting the physiological detection signal from the physiological signal detector to the Bluetooth module 2 or the Wi-Fi module 2a at the detection end;

S03: the Bluetooth module 2 or the Wi-Fi module 2a at the detection end intended to transmit the physiological detection signal;

S04: utilizing the mobile phone 3 equipped with the built-in Bluetooth module 4 or the built-in Wi-Fi module 4a of the subject to receive the physiological detection signal; and S05: creating a message containing a data transmission command and a data format protocol by encoding the physiological detection signal through the mobile phone of the subject, then transmitting the message or the App ID 7 to the mobile phone 5 of the caretaker, the physiological signal detector 1 installed with a plurality of phone numbers of the mobile phone 5 of the caretaker.

In accordance with the above-mentioned steps, the data transmission command and the data format protocol transmitted through the physiological signal detector 1 to the Bluetooth module 2 at the detection end and the built-in Bluetooth module 4, or to the Wi-Fi module 2a at the detection end and the Wi-Fi module 4a are specifically defined.

Command initiation of the present invention is defined as DD-, which is combined with an additional term to indicate a command operation name and a content format. The command initiation is intended to initiate operations of transmitting messages, transmitting a string, and transmitting physiological detection values including oximeter density, sphygmomanometer values, glucose meter values, and physiological detection signal. An operation item of the present invention or a transmitting item transmitted by the physiological signal detector 1 is capable of being defined by the command operation name. The content format is intended to define a data format of a command operation.

Further to above description, in a preferable embodiment, the term "DD-SEND command" is utilized to express an operation of transmitting a message to a mobile phone, wherein SEND is defined as a command operation name for transmitting the message, which is followed by mobile phone numbers.

"DD-SEND, Mobile Phone No." represents that the physiological signal detector 1 is intended to transmit a message containing the phone number of the mobile phone 5 of a remote caretaker through the UART 6 and the ASCII code to the Bluetooth module 2 at the detection end and the built-in Bluetooth module 4, or to the Wi-Fi module 2a at the detection end and the built-in Wi-Fi module 4a, wherein a corresponding command format is: DD-SEND, Mobile Phone No. <CR>.

Taking DD-SEND, 0935000000 for example: in respect of content of the ASCII code of the UART 6, a corresponding connection is as follows:
D hexadecimal ACSII code is 44
- hexadecimal ACSII code is 2D
S hexadecimal ACSII code is 33
E hexadecimal ACSII code is 45

In analogy, the ASCII code transmitted through the UART 6 is: 44442D53454E442C303935303030303030300D.

Accordingly, the Bluetooth module 2 at the detection end and the built-in Bluetooth module 4, or the Wi-Fi module 2a at the detection end and the built-in Wi-Fi module 4a are capable of transmitting a message to the mobile phone 5 (0935000000) of the remote caretaker according to a command of the physiological signal detector 1.

Define DD-STR command as "transmitting a string", wherein STR is defined as the command operation name, which is followed by string data, DD-STR representing "transmitting a string".

Accordingly, the physiological signal detector 1 is capable of transmitting the string to the Bluetooth module 2 at the detection end and the built-in Bluetooth module 4, or to the Wi-Fi module 2a at the detection end and the built-in Wi-Fi module 4a through the UART 6.

Furthermore, when the content of the string is abcdefghijklmnopqrstu, a corresponding command format is presented as: DD-STR, abcdefghijklmnopqrstu<CR>, wherein the ASCII code is: 44442D5354522C6162636465666768696A6B6C6D6E6F7071727 374750D. In combination with DD-SEND, Mobile Phone No., the mobile phone 5 of the remote caretaker is to receive a message indicated as abcdefghijklmnopqrstu.

Define OXI as a command operation name of transmitting oximeter 14 density, which is followed by detection information about the oximeter 14; therefore, "DD-OXI, SpO2, Pulse Rate" represents transmitting blood oxygen density and pulse rate of the oximeter 14.

The oximeter 14 is capable of transmitting the blood oxygen density and pulse rate being detected to the Bluetooth module 2 at the detection end and the built-in Bluetooth module 4, or to the Wi-Fi module 2a at the detection end and the built-in Wi-Fi module 4a through the UART 6. When the blood oxygen density and the pulse rate are respectively shown as 100.00, 75.00, a corresponding command format thereof is presented as: DD-OXI, 100.00, 075.00<CR>, and the ASCII code is presented as: 44442D4F58492C3130302E30302C3037352E30300D. In combination with DD-SEND, Mobile Phone No., the mobile phone 5 of the remote caretaker is to receive a message indicated as:
Oximeter
SpO2 100%
Pulse Rate 75 bpm Define BP as a command operation name of transmitting sphygmomanometer 13 values, which is followed by the sphygmomanometer 13 detection values; "DD-BP Systolic, Diastolic, Pulse Rate" represents transmitting systolic pressure, diastolic pressure, and a pulse rate detected by the sphygmomanometer 13.

The sphygmomanometer 13 is capable of transmitting the systolic pressure, the diastolic pressure, and the pulse rate being detected to the Bluetooth module 2 at the detection end and the built-in Bluetooth module 4, or to the Wi-Fi module 2a at the detection end and the built-in Wi-Fi module 4a through the UART 6. When the systolic pressure, the diastolic pressure, and the pulse rate are respectively shown as 120.00, 080.00, 75.00, a corresponding command format thereof is presented as: DD-BP, 120.00, 080.00, 75.00 <CR>, and the ASCII code is as follows: 4442D42502C31323 02E30302C3038302E303037352E30300D. In combination with DD-SEND, Mobile Phone No., the mobile phone 5 of the remote caretaker is to receive a message indicated as:
Blood Pressure
Systolic 120 mmHg
Diastolic 80 mmHg
Pulse Rate 75 bpm As mentioned above, DD-Command is utilized to define a command operation item for transmitting the message containing the physiological detection signal. Alternatively, DD-STR is capable of being utilized to transmit content of a string as required. For example, when the physiological signal detector 1 is intended to transmit:
Oximeter
SpO2 100%
Pulse Rate 75 bpm
It is capable of utilizing STR Command to transmit content of the string to the Bluetooth module 2 at the detection end and the built-in Bluetooth module 4, or to the Wi-Fi module 2a at the detection end and the built-in Wi-Fi module 4a through the UART 6 and the ASCII code, wherein a corresponding command format and ASCII are as follows:
DD-STR, Oximeter<CR>
44442D5354522C4F78696D657465720D
DD-STR, SpO2 100%<CR>
44442D5354522C53704F322031303020250D
DD-STR, Pulse Rate 75 bpm<CR>
44442D5354522C50756C73652052617465203735206
2706D0D Alternatively, when the physiological signal detector 1 is intended to transmit:
Blood Pressure
Systolic 120 mmHg
Diastolic 80 mmHg
Pulse Rate 75 bpm
It is capable of utilizing STR Command to transmit content of the string to the Bluetooth module 2 at the detection end and the built-in Bluetooth module 4, or to the Wi-Fi module 2a at the detection end and the built-in Wi-Fi module 4a through the UART 6 and the ASCII code, wherein a corresponding command format and ASCII are as follows:
DD-STR, Blood Pressure<CR>
44442D5354522C426C6F6F6420507265737375265200D
DD-STR, Systolic 120 mmHg<CR>
44442D5354522C537973746F6C696320313230206D6D48670D
DD-STR, Diastolic 80 mmHg<CR>
44442D5354522C44696173746F6C69632038302006D6D48670D
DD-STR Pulse Rate 75 bpm
44442D5354522C50756C73652052617465203735206
2706D0D

TABLE 4 command and data format

| Operation Item | Command Initiation | Command Operation | Content Format |
| --- | --- | --- | --- |
| Transmitting a message | DD- | SEND | Mobile Phone No. or Pmart Phone App ID |
| Transmitting a string | DD- | STR | String |
| Transmitting oximeter density | DD- | OXI | SpO2, Pulse Rate |
| Transmitting sphygmomanometer values | DD- | BP | Systolic, Diastolic, Pulse Rate |

It is noted that the method of the present invention for defining the command format and the data format is also capable of defining other physiological signal detectors not mentioned above or other applicable transmitting operation items and content formats.

The method of the present invention is to utilize the physiological signal detector 1, the Bluetooth module 2 at the detection end, the built-in Bluetooth module 4 interface standard, the data transmission command and the data format protocol, or in another embodiment the method utilizes the physiological signal detector 1, the Wi-Fi module 2 at the detection end, the built-in Wi-Fi module 4a interface standard, the data transmission command and the data format protocol, to create a communication standard cross the ICT industry and medical instruments for enabling rapid combination of cross-industry technique advantages and cooperation of dissimilar industries, improving the development of medical electronic products, and improving the added value of production.

Accordingly, the method of present invention enables patients or elders in need of daily care to detect their physiological state by using the clinical thermometer 11, the glucose meter 12, the sphygmomanometer 13, the pulse meter, or the oximeter and other physiological signal detectors 1 generating the physiological detection signal, which is to be transmitted in a manner of sending a message to a mobile phone of a caretaker (such as, for example, relatives, doctors, or nurses) or to a communication device of a medical unit (e.g. hospital) so as to instantly indicate a physiological state of a subject and to provide appropriate care without requiring additional data transmission apparatus.

The method of the present invention is to utilize the physiological signal detector 1 in combination with the Bluetooth module 2 or the Wi-Fi module 2a at the detection end to function as a detection module that is miniaturized, portable, digital, wireless, and easily operated. Furthermore, the above-mentioned detection module is communicable with the Bluetooth module 4 or the Wi-Fi module 4a of the mobile phone 3 of the subject. In this manner, the method of the present invention is further intended to transmit the physiological detection signal in a manner of sending the message or the App ID message to the mobile phone of the caretaker through a regular daily used mobile phone, whereby instantly providing the physiological state for the caretaker.

Figure 7:
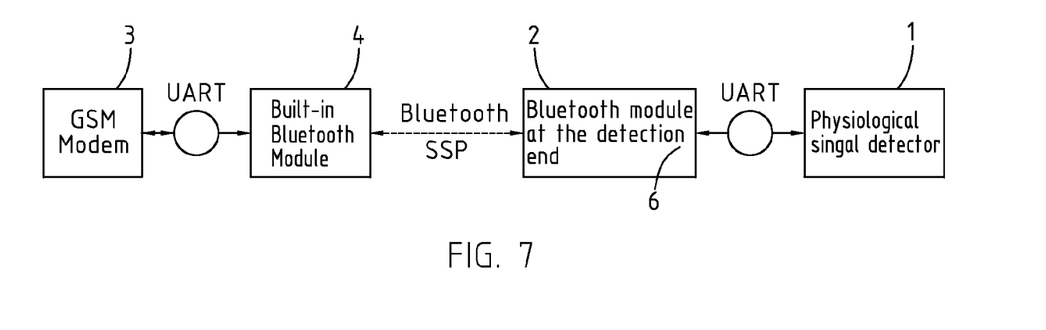
FIG. 7 is a schematic diagram exemplifying the method of FIG. 6.

Please refer to FIG. 7 showing a schematic diagram exemplifying the method of the present invention. The Bluetooth module 2 is built with a CSR BC417143B chip, and the home used physiological signal detector 1 is exemplified by the sphygmomanometer 13 of the model no. P10.

Figure 8:
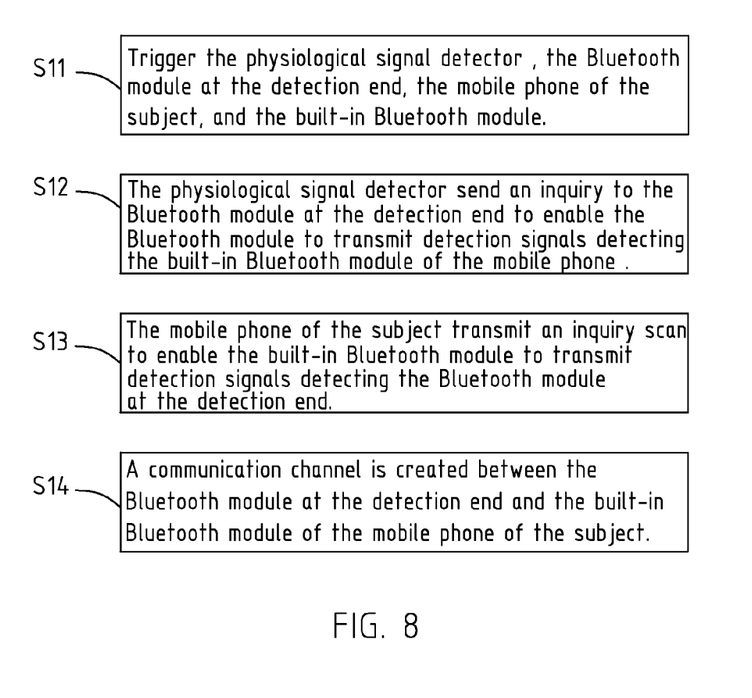
FIG. 8 is another schematic flow chart of the method of FIG. 6.

Referring to FIG. 8, the method for transmitting physiological detection signal through the physiological signal detector 1, the Bluetooth module 2 at the detection end, the mobile phone 3 (GSM modem) of the subject, and the built-in Bluetooth module 4, comprises the steps:

S11: trigger the physiological signal detector 1, the Bluetooth module 2 at the detection end, the mobile phone 3 of the subject, and the built-in Bluetooth module 4;

S12: the physiological signal detector 1 sends an inquiry to the Bluetooth module 2 at the detection end to enable the Bluetooth module 2 to transmit detection signals detecting the built-in Bluetooth module 4 of the mobile phone 3;

S13: the mobile phone 3 of the subject transmit an inquiry scan to enable the built-in Bluetooth module 4 to transmit detection signals detecting the Bluetooth module 2 at the detection end; and S14: a BT SPP Ready communication channel is created between the Bluetooth module 2 at the detection end and the built-in Bluetooth module 4 of the mobile phone 3 of the subject.

Figure 9:
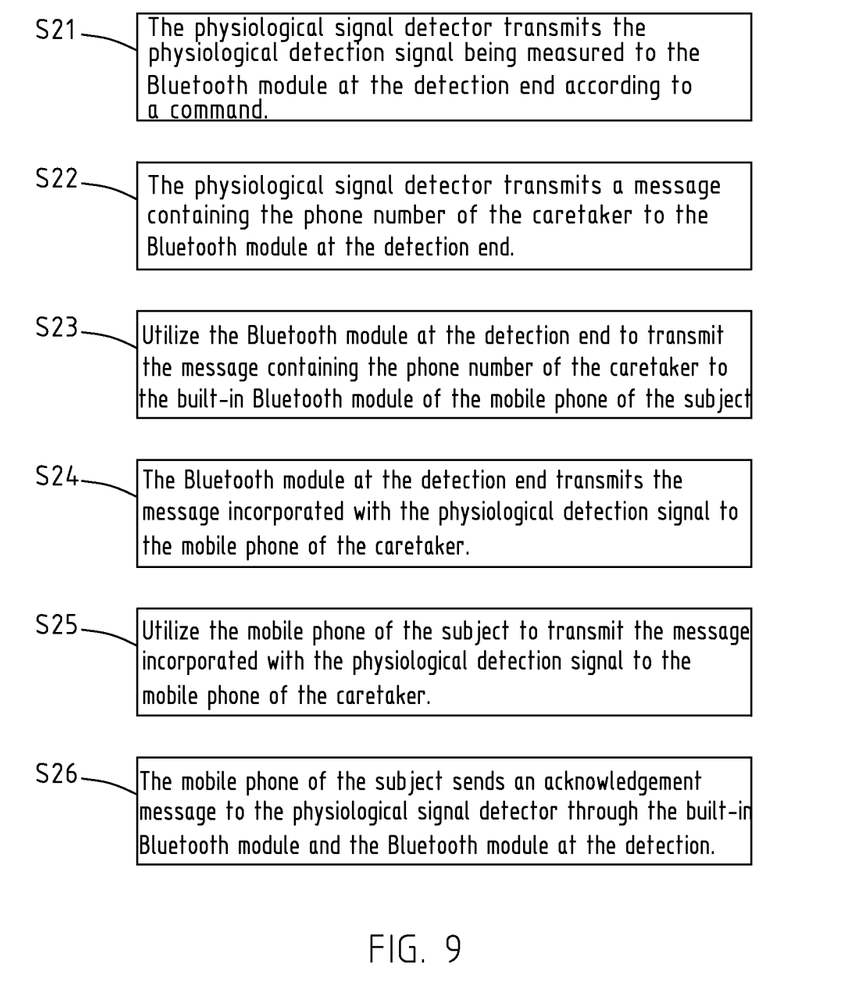
FIG. 9 is another schematic flow chart of the method of FIG. 6.

In another example of the method of the present invention, the differences are that the Bluetooth module 2 at the detection end is replaced with the Wi-Fi module 2a, and the built-in Bluetooth module 4 is replaced with the built-in Wi-Fi module 4a where other steps remain the same. Referring to FIG. 9, after the BT SPP Ready communication channel is created between the Bluetooth module 2 at the detection end and the built-in Bluetooth module 4 of the mobile phone 3 of the subject, the physiological signal detector 1 is capable of transmitting the phone number of the mobile phone 5 of the caretaker and the physiological detection signal being detected to the built-in Bluetooth module 4 of the mobile phone 3 of the subject through the Bluetooth module 2 at the detection end, and then the built-in Bluetooth module 4 of the mobile phone 3 is capable of transmitting the message to the mobile phone 5 of the remote caretaker, wherein the steps of transmission are as follows:

S21: the P10 sphygmomanometer 13 which functions as the physiological signal detector 1 transmits the physiological detection signal containing the blood pressure value being measured to the Bluetooth module 2 at the detection end according to a command and a message of DD-STR or DD-BP that is transmitted through the UART 6;

S22: the physiological signal detector 1 transmits a message of DD-SEND Mobile Phone No. containing the phone number of the caretaker to the Bluetooth module 2 at the detection end;

S23: utilize the Bluetooth module 2 at the detection end to transmit a message of command (AT CMGS Mobile Phone No.) containing the phone number of the mobile phone 5 to the built-in Bluetooth module 4 of the mobile phone 3 of the subject;

S24: the Bluetooth module 2 at the detection end transmits the message containing the physiological detection signal to the built-in Bluetooth module 4 of the mobile phone 3 of the subject so that the physiological detection signal is being received by the Bluetooth module 4 of the mobile phone 3;

S25: utilize the mobile phone 3 to incorporate the physiological detection signal into the message, and the mobile phone 3 dials the phone number of the mobile phone 5 of the caretaker according to the command so as to send the message incorporated with the physiological detection signal to the mobile phone 5 of the remote caretaker; and S26: the mobile phone 3 of the subject further sends an acknowledgement message to the physiological signal detector 1 through the built-in Bluetooth module 4 and the Bluetooth module 2 at the detection end for acknowledging that the message incorporated with the physiological detection signal is being sent to the mobile phone of the caretaker so as to complete processes of the method.

In respect of detection process of the built-in Bluetooth module 4 of the mobile phone 3, the Bluetooth module 2 (CSR BC417143B chip module) at the detection end, and the physiological signal detector 1 (P10 sphygmomanometer 13), the physiological signal detector 1 is capable of automatically transmitting the message to the mobile phone 5 of the remote caretaker through the Bluetooth module 2 at the detection end and the built-in Bluetooth module 4 of the mobile phone 3 as soon as the physiological detection signal is detected.

Alternatively, the physiological signal detector 1 is capable of transmitting the phone number of the mobile phone 5 of the caretaker and the physiological detection signal to the built-in Wi-Fi module 4a of the mobile phone 3 of the subject through the Wi-Fi module 2a at the detection end, and then the message is sent through the built-in Wi-Fi module 4a to the mobile phone 5 of the caretaker, wherein the processes of transmission in this example differ from that of the above-mentioned embodiment in which the Bluetooth module 2 at the detection end is replaced with the Wi-Fi module 2a at the detection end, and the built-in Bluetooth module 4 is replaced with the built-in Wi-Fi module 4a.

Figure 10:
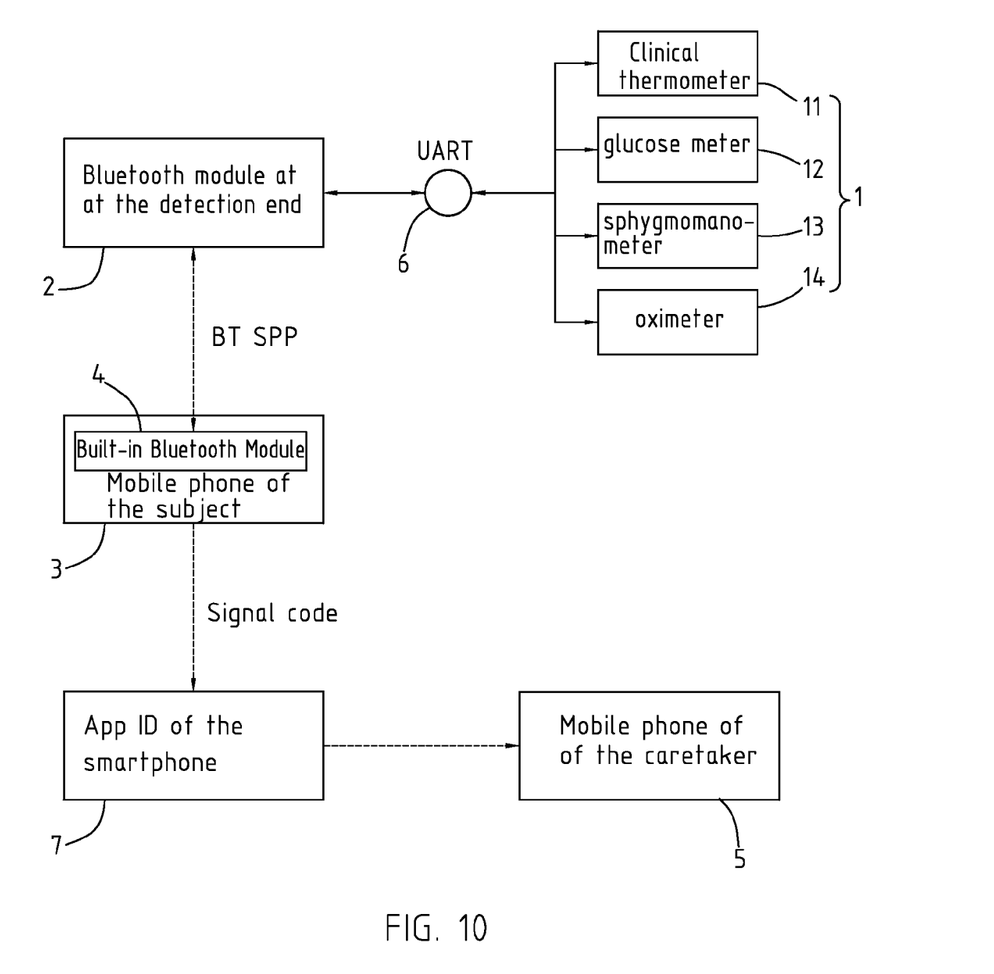
FIG. 10 is a schematic block diagram showing a configuration of a method in accordance with a second embodiment of the present invention.
Figure 11:
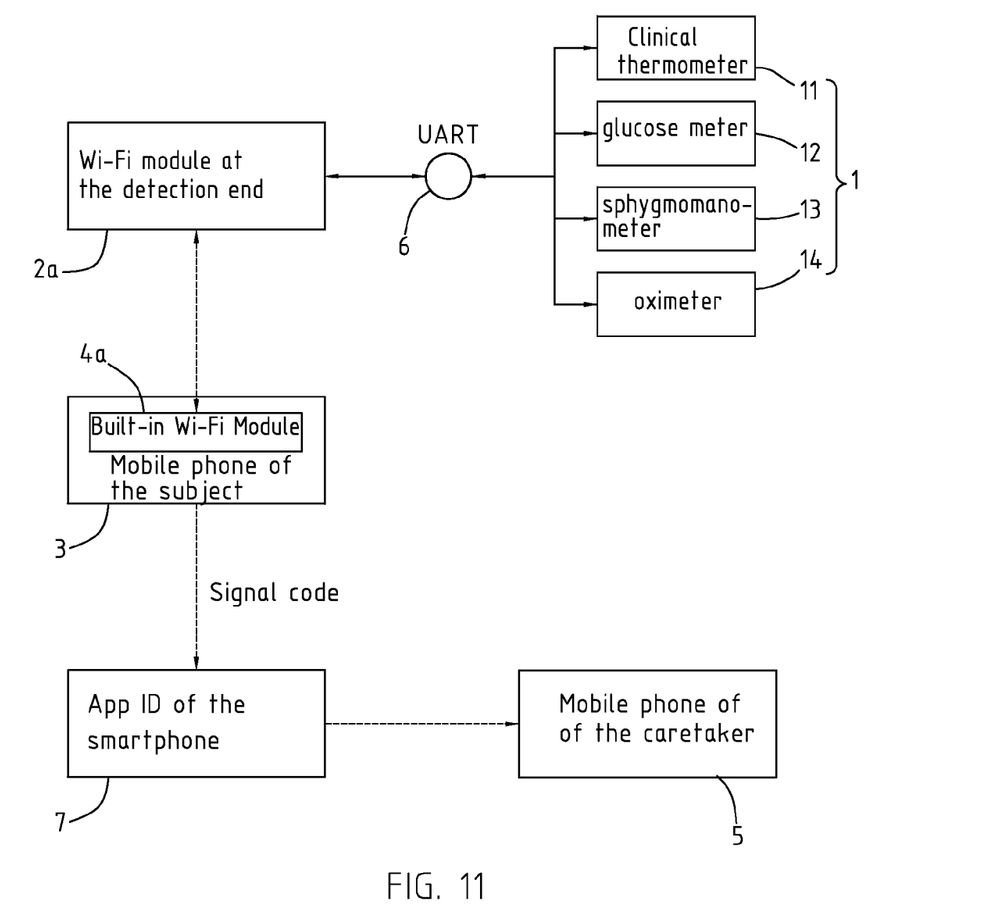
FIG. 11 is a schematic block diagram showing another example of the configuration of FIG. 10.

Referring to FIG. 10 showing a schematic block diagram that illustrates a configuration of the method in accordance with a second embodiment of the present invention, in combination with FIG. 11 showing the method for transmitting physiological detection signals through a mobile phone device and a Bluetooth/Wi-Fi communication system, the method of the second embodiment comprises:

provide at least one the physiological signal detector 1 for performing a physiological examination on a subject so as to generate at least one physiological detection signal;

provide a communication interface for transmitting the physiological detection signal from the physiological signal detector to the Bluetooth module 2 or the Wi-Fi module 2a at a detection end;

the Bluetooth module 2 or the Wi-Fi module 2a at the detection end is intended to transmit the physiological detection signal;

utilize the mobile phone 3 equipped with the built-in Bluetooth module 4 or the Wi-Fi module 4a of the subject to receive the physiological detection signal; and create a signal code containing a data transmission command and a data format protocol by encoding the physiological detection signal through the mobile phone 3 of the subject, then transmitting the signal code to an App ID of a smartphone so as to be allowed to be downloaded to the mobile phone 5 of the caretaker.

In this manner, the physiological detection signal is incorporated into the signal code through the mobile phone 3 of the subject and is then transmitted to the App ID 7 of the smartphone. The mobile phone 3 of the subject further sends an acknowledgement message to the physiological signal detector 1 through the Bluetooth module 2 or the Wi-Fi module 2a at the detection end for acknowledging that the signal code incorporated into the physiological detection signal is being sent to the App ID 7 of the smartphone so as to complete processes of the method.

Accordingly, the method of the present invention utilizes the three interfere standards of the UART, the Bluetooth or Wi-Fi, and the mobile phone standard data to set a transmission platform for the physiological signal detector, so as to transmit the physiological detection signal being detected and measured in a manner of sending a message or a signal code to a receiving end of a target through the UART, the data transmission command and the data format protocol, the Bluetooth or Wi-Fi module, and the mobile phone device.

It is understood that the invention may be embodied in other forms within the scope of the claims. Thus the present examples and embodiments are to be considered in all respects as illustrative, and not restrictive, of the invention defined by the claims.

What is claimed is:

1. A method for transmitting physiological detection signals through a mobile phone device and a Bluetooth communication system, comprising:

providing at least a physiological signal detector for performing a physiological examination on a subject so as to generate at least one physiological detection signal;

providing a communication interface for transmitting the physiological detection signal from the physiological signal detector to a Bluetooth module at a detection end;

the Bluetooth module at the detection end intended to transmit the physiological detection signal;

utilizing a mobile phone equipped with a built-in Bluetooth module of the subject to receive the physiological detection signal; and creating a message containing a data transmission command and a data format protocol by encoding the physiological detection signal through the mobile phone of the subject, then transmitting the message to a mobile phone of a caretaker, or creating a signal code containing a data transmission command and a data format protocol by encoding the physiological detection signal through the mobile phone of the subject, then transmitting the signal code to an application (App) identification (ID) of a smartphone so as to be allowed to be downloaded to the mobile phone of the caretaker;

wherein the mobile phone of the subject is further intended to incorporate the physiological detection signal into the message and to transmit the message to the mobile phone of the caretaker, and then sending an acknowledgement message to the physiological signal detector through the Bluetooth module at the detection end for acknowledging that the message containing the physiological detection signal is being sent to the mobile phone of the caretaker.

2. The method of claim 1, wherein the data transmission command and the data format protocol are created based on a communication standard of ASCII.

3. The method of claim 1, wherein the data transmission command and the data format protocol comprise command initiation, command operation, and content format, the command initiation is intended to initiate operations of transmitting a message, transmitting a string, and transmitting physiological detection values including oximeter density, sphygmomanometer values, glucose meter values, and physiological detection signals.

4. The method of claim 1, wherein the physiological signal detector is intended to enable the Bluetooth module at the detection end to detect the built-in Bluetooth module of the mobile phone of the subject, and the mobile phone of the subject is intended to enable the built-in Bluetooth module to detect the Bluetooth module at the detection end so as to allow the Bluetooth module at the detection end and the built-in Bluetooth module of the mobile phone of the subject to communicate with each other.

5. The method of claim 1, wherein the physiological signal detector is stored with phone numbers of the mobile phone of the caretaker, and is intended to transmit the physiological detection signal and the phone numbers of the caretaker to the built-in Bluetooth module of the mobile phone of the subject through the Bluetooth module at the detection end, whereby enabling the mobile phone of the subject to call the phone numbers of the caretaker or the App ID of the smartphone according to a commander, the physiological signal detector transmitting the at least one physiological detection signal with a predetermined order and the phone numbers of the caretaker to the Bluetooth module at the detection end.

6. The method of claim 1, wherein the Bluetooth module at the detection end and the built-in Bluetooth module of the mobile phone of the subject are respectively communicated based on Standard BT 2.0+EDR Class II.

7. The method of claim 1, wherein the Bluetooth module at the detection end is electrically connected to the physiological signal detector, and the communication interface is a universal asynchronous receiver/transmitter.

8. A method for transmitting physiological detection signals through a mobile phone device and a Wi-Fi communication system, comprising:

providing at least a physiological signal detector for performing a physiological examination on a subject so as to generate at least one physiological detection signal;

providing a communication interface for transmitting the physiological detection signal from the physiological signal detector to a Wi-Fi module at a detection end;

the Wi-Fi module at the detection end intended to transmit the physiological detection signal;

utilizing a mobile phone equipped with a built-in Wi-Fi module of the subject to receive the physiological detection signal; and creating a message containing a data transmission command and a data format protocol by encoding the physiological detection signal through the mobile phone of the subject, then transmitting the message to a mobile phone of a caretaker, or creating a signal code containing a data transmission command and a data format protocol by encoding the physiological detection signal through the mobile phone of the subject, then transmitting the signal code to an application (App) identification (ID) of a smartphone so as to be allowed to be downloaded to the mobile phone of the caretaker;

wherein the mobile phone of the subject is further intended to incorporate the physiological detection signal into the signal code and to transmit the signal code to the App ID of the smartphone, and then sending an acknowledgement message to the physiological signal detector through the Wi-Fi module at the detection end for acknowledging that the signal code containing the physiological detection signal is being sent to the App ID of the smartphone.

9. The method of claim 8, wherein the data transmission command and the data format protocol are created based on a communication standard of ASCII.

10. The method of claim 8, wherein the data transmission command and the data format protocol comprise command initiation, command operation, and content format, the command initiation is intended to initiate operations of transmitting a message, transmitting a string, and transmitting physiological detection values including oximeter density, sphygmomanometer values, glucose meter values, and physiological detection signal.

11. The method of claim 8, wherein the physiological signal detector is intended to enable the Wi-Fi module at the detection end to detect the built-in Wi-Fi module of the mobile phone of the subject, and the mobile phone of the subject is intended to enable the built-in Wi-Fi module to detect the Wi-Fi module at the detection end so as to allow the Wi-Fi module at the detection end and the built-in Wi-Fi module of the mobile phone of the subject to communicate with each other.

12. The method of claim 8, wherein the physiological signal detector is stored with phone numbers of the mobile phone of the caretaker, and is intended to transmit the physiological detection signal and the phone numbers of the caretaker to the built-in Wi-Fi module of the mobile phone of the subject through the Wi-Fi module at the detection end, whereby enabling the mobile phone of the subject to call the phone numbers of the caretaker or the App II) of the smartphone according to a commander, the physiological signal detector transmitting the at least one physiological detection signal with a predetermined order and the phone numbers of the caretaker to the Wi-Fi module at the detection end.

13. The method of claim 8, wherein the Wi-Fi module at the detection end is electrically connected to the physiological signal detector, and the communication interface is a universal asynchronous receiver/transmitter.

* * * * *